(12) United States Patent
Cioncoloni et al.

(10) Patent No.: US 11,154,407 B2
(45) Date of Patent: Oct. 26, 2021

(54) DEVICE FOR ENHANCING A SUBJECT'S GRASPING CAPABILITY

(71) Applicant: UNIVERSITA' DEGLI STUDI DI SIENA, Siena (IT)

(72) Inventors: David Cioncoloni, Monteriggioni (IT); Irfan Hussain, Pindi Bhattian (PK); Domenico Prattichizzo, Siena (IT); Simone Rossi, Siena (IT); Gionata Salvietti, Citta' Marciano Della Chiana (IT); Giovanni Spagnoletti, Molinara (IT)

(73) Assignee: UNIVERSITA' DEGLI STUDI DI SIENA, Siena (IT)

( * ) Notice: Subject to any disclaimer, the term of this patent is extended or adjusted under 35 U.S.C. 154(b) by 451 days.

(21) Appl. No.: 16/076,064

(22) PCT Filed: Feb. 9, 2017

(86) PCT No.: PCT/IB2017/050725
§ 371 (c)(1),
(2) Date: Aug. 7, 2018

(87) PCT Pub. No.: WO2017/137930
PCT Pub. Date: Aug. 17, 2017

(65) Prior Publication Data
US 2021/0052399 A1    Feb. 25, 2021

(30) Foreign Application Priority Data
Feb. 9, 2016   (IT) .......................... 102016000013321

(51) Int. Cl.
*A61F 2/54*    (2006.01)
*A61F 2/78*    (2006.01)
(Continued)

(52) U.S. Cl.
CPC ................ *A61F 2/586* (2013.01); *A61F 2/54* (2013.01); *A61F 2/70* (2013.01); *A61F 2/78* (2013.01);
(Continued)

(58) Field of Classification Search
CPC .... A61F 2/586; A61F 2/78; A61F 2/70; A61F 2/54; B25J 13/00
See application file for complete search history.

(56) References Cited

U.S. PATENT DOCUMENTS

| 9,004,559 B2 | 4/2015 | Claffee et al. |
| 10,561,507 B1* | 2/2020 | Asada ........................ A61F 2/70 |
| 2020/0170873 A1* | 6/2020 | Walsh ....................... B25J 9/142 |

OTHER PUBLICATIONS

International Search Reported, dated Jun. 21, 2017, corresponding to Application PCT/IB2017/050725.
(Continued)

*Primary Examiner* — Bruce E Snow
(74) *Attorney, Agent, or Firm* — Ladas & Parry LLP; Malcolm J. MacDonald

(57) ABSTRACT

A device for enhancing a user's grasping capability comprises a belt-like support configured to be tightly fitted about a user's part of the body; an articulated gripping element having a plurality of phalanxes: proximal, fixed to the support, intermediate and distal, which are articulated to each other by articular joints; a motor unit fixed to the support; a winding drum; a tendon partially wound on the drum and extending along the phalanxes and the joints, arranged so that, by pulling it from the drum, the phalanxes rotate about respective articular joints and move the articulated gripping element from an extended position to a gripping bow-shaped position, causing a flexion/extension movement of the articulated gripping element, the joints configured so that by releasing the tendon from the drum, the phalanxes rotate about the respective joints and move the
(Continued)

articulated gripping element between gripping bow-shaped position and extended position.

18 Claims, 7 Drawing Sheets

(51) Int. Cl.
    *A61F 2/70* (2006.01)
    *A61F 2/58* (2006.01)
    *A61F 2/50* (2006.01)
    *A61F 2/68* (2006.01)

(52) U.S. Cl.
    CPC ............. *A61F 2002/5007* (2013.01); *A61F 2002/6818* (2013.01); *A61F 2002/6827* (2013.01); *A61F 2002/6854* (2013.01); *A61F 2002/701* (2013.01); *A61F 2002/704* (2013.01); *A61F 2002/707* (2013.01); *A61F 2002/7856* (2013.01); *A61F 2002/7862* (2013.01)

(56) References Cited

OTHER PUBLICATIONS

Hussain, Irfan, et al., Design Guidelines for a Wearable Robotic Extra-Finger, 2015 IEEE 1st International Forum On Research and Technologies for Society and Industry Leveraging a Better Tomorrow, (RTSI). IEEE, Sep. 16, 2015 (Sep. 16, 2015), pp. 54-60. XP032805853.

Hussain, Irfan, et al., "The Soft-SixthFinger: a Wearable EMG Controlled Robotic Extra-Finger for Grasp Compensation in Chronic Stroke Patients", IEEE Robotics and Automation Letters, IEEE, vol. 1, No. 2, Jul. 1, 2016 (Jul. 1, 2016), pp. 1000-1006. XP011602415.

Pacchierotti, Claudio, et al., The hRing: a Wearable Haptic Device to Avoid Occlusions in Hand Tracking, 2016 IEEE Haptics Symposium (Haptics), IEEE, Apr. 8, 2016 (Apr. 8, 2016), pp. 134-139. XP032897170.

Wu, Faye Y., et al., "'Hold-and-Manipulate' with a Single Hand Being Assisted by Wearable Extra Fingers", 2015 IEEE International Conference On Robotics and Automation (ICRA), May 30, 2015 (May 30, 2015), pp. 6205-6212. XP055322693.

Salvietti, Gionata, "The Robotic Sixth Finger: a Wearable CompensatoryTool to Regain Grasping Capabilities in Paretic Hand", Sep. 1, 2015 (Sep. 1, 2015). XP055322675.

Hussain, Irfan, et al., "Vibrotactile Haptic Feedback for Intuitive Control of Robotic Extra Fingers", 2015 IEEE World Haptics Conference (WHC), Jun. 1, 2015 (Jun. 1, 2015), pp. 394-399. XP055322678.

Sobajima, Masafumi, et al., "Improvement of Operability of Extra Robotic Thumb Using Tactile Feedback by Electrical Stimulation", 2015 International Symposium On Micro-Nanomechatronics and Human Science (MHS), IEEE, Nov. 23, 2015 (Nov. 23, 2015), pp. 1-3. XP032885488.

\* cited by examiner

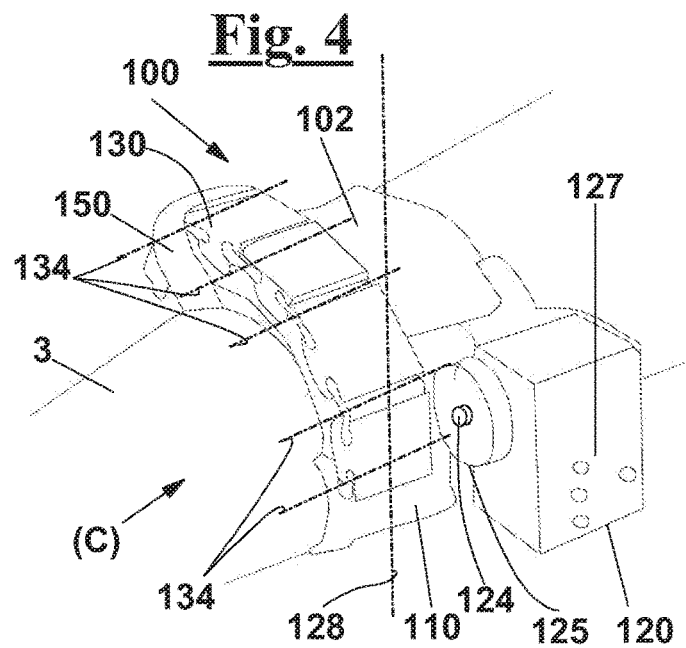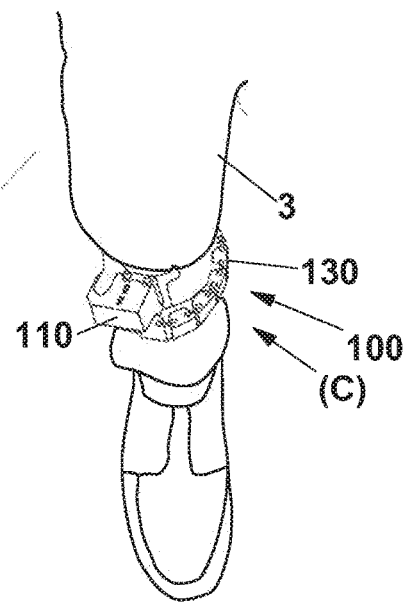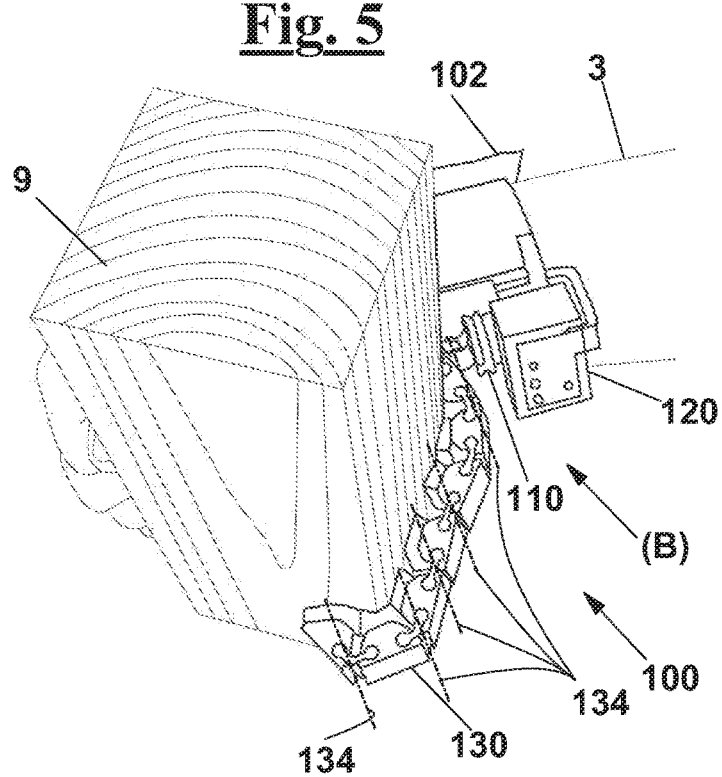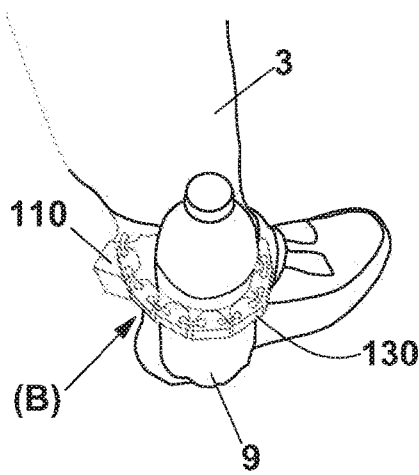

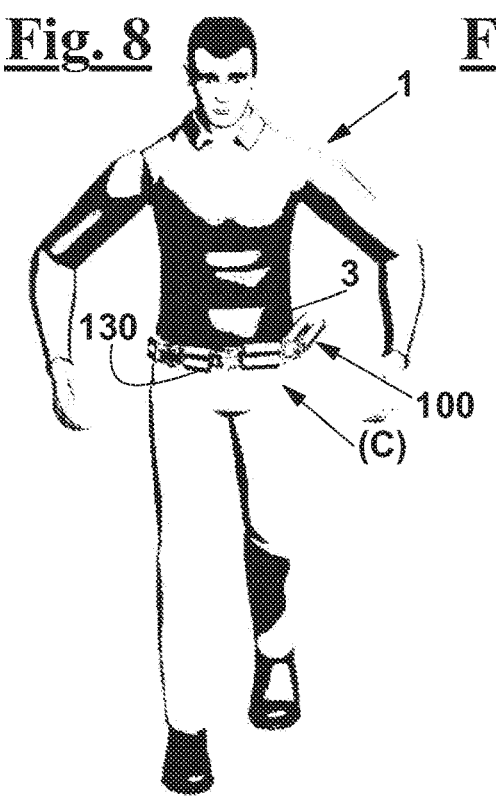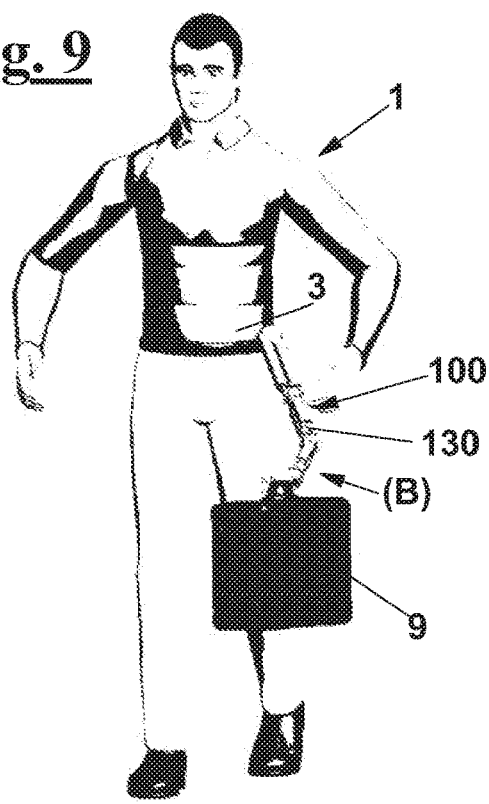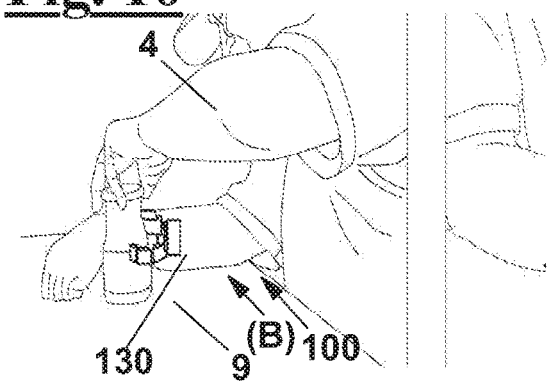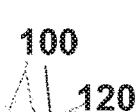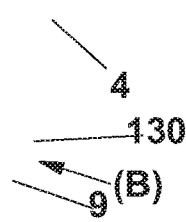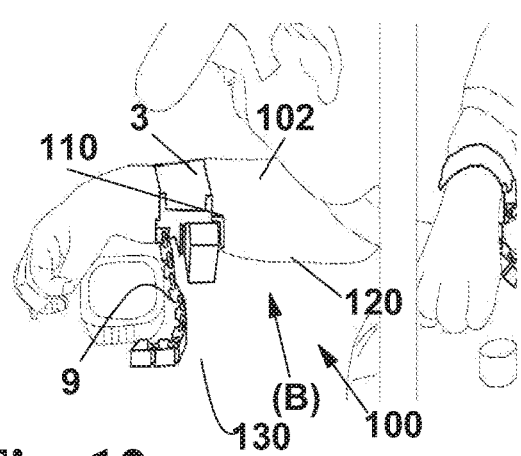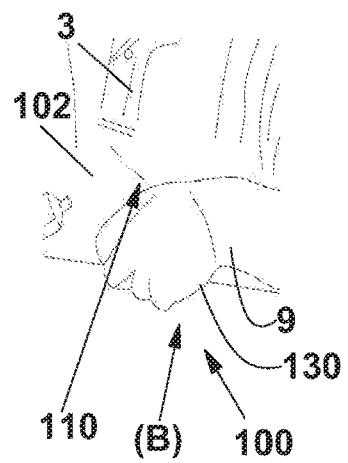

DEVICE FOR ENHANCING A SUBJECT'S GRASPING CAPABILITY

FIELD OF THE INVENTION

The present invention relates to a robotic device that can be worn on a limb or on a different part of a user's body. For example, the device can be a sixth finger for a hand or for a foot, or an additional gripping limb, to be worn on a forearm, on the ankle, on the waist and the like.

Moreover, the invention relates to such a robotic device for rehabilitation purposes.

PRIOR ART

An auxiliary robotic finger or "sixth finger" for a user's hand, to enhance his/her capacity, is disclosed in D. Prattichizzo, M. Malvezzi, I. Hussain, G. Salvietti, *The Sixth-Finger: a Modular Extra-Finger to Enhance Human Hand Capabilities*. In Proc. IEEE Int. Symp. in Robot and Human Interactive Communication, pages 993-998, Edinburgh, United Kingdom, 2014, incorporated here by reference.

More in detail, this device serves to making a human hand more symmetric, and is configured in such a way that, when the fingers human are closed, i.e. when the phalanxes of the fingers perform a flexion movement, the auxiliary finger emulate this movement. This device also makes it possible to enlarge the hand workspace and to enhance its grip capacities. Such robotic finger is a modular finger that can be worn on the wrist by means of a rubber belt.

The structure of the modular portion is obtained using quick prototyping techniques, whereas the active degrees of freedom are made with servomotors. Concerning the control, the movement of the human hand is captured by a data glove and is mapped on an auxiliary finger by a dedicated algorithm described in D. Prattichizzo, G. Salvietti, F. Chinello, M. Malvezzi, *An Object-based Mapping Algorithm to control Wearable Robotic Extra-Fingers*, in Proc. IEEE/ASME Int. Conf. On Advanced Intelligent Mechatronics, pages 1563-1568, Besancon, France, 2014, incorporated here by reference.

In I. Hussain, G. Salvietti, L. Meli, C. Pacchierotti, D. Prattichizzo, *Using the robotic sixth finger and vibrotactile feedback for grasp compensation in chronic stroke patients*, in Proc. IEEE/RAS-EMBS International Conference on Rehabilitation Robotics (ICORR), Singapore, Republic of Singapore, 2015, also incorporated by reference, a first application thereof is described to assisting patients having a hemiparetic limb.

In Wu, Faye Y., and Harry Asada, *Bio-artificial synergies for grasp posture control of supernumerary robotic fingers* (2014), a gripping device is described to be worn on a forearm of a user, whose grip movement can be controlled through the device by sensors arranged on the hand.

Hussain Irfan et al., *Design guidelines to wearable robotic extra-finger*, 2015 IEEE 1st International Forum on Research and Technologies for society and industry leveraging to better tomorrow (RTSI), IEEE 16 Sep. 2015, pages 54-60, describes a hand additional finger that has a first motor for actuating a flexion movement thereof by a tendon partially wound on a winding pulley controlled by the motor, and that can be arranged about the wrist in a rest position like a bracelet when it is not used. In this device, the rest position is obtained by a dedicated motor. In the rest position, the first motor is used for bringing the additional finger in a grip-like position, in order to arrange it about the wrist.

SUMMARY OF THE INVENTION

It is a feature of the present invention to provide a minimum-size and weight robotic finger for a user, with respect to the prior art devices, which can be therefore worn more comfortably.

It is also a feature of the invention to provide such a device that do not hinder the normal movements of a user's limb, when it is not used.

It is also a feature of the invention to provide such a device that enables rehabilitation exercises for a user with a limb disability due to a trauma or to a cerebrovascular disease, such as a stroke, or to a different disease.

It is also a feature of the invention to provide such a device that can be worn on limbs or on different user's body parts, in order to enhance his/her grip capacities.

These and other objects are achieved by a device for enhancing a user's grasping capability, comprising:

- a belt-like support configured to be tightly fitted about a part of the body of the user, the belt-like support having a longitudinal axis;
- at least one articulated gripping element having a plurality of phalanxes serially connected to each other about respective joint axes parallel to one another, the phalanxes comprising a proximal phalanx, connected to the support, and a distal phalanx, the phalanxes articulated to each other by so articular joints;
- a motor unit fixed to the support;
- a winding drum connected to the motor unit between an actuation condition and a release condition;
- at least one tendon partially wound on the winding drum and partially extending through the phalanxes and the articular joints, the tendon arranged in such a way that, if the tendon is pulled by the winding drum in said actuation condition, the phalanxes rotate about respective articular joints and move the articulated gripping element from an extended position to a gripping bow-shaped position, causing a flexion/extension movement of the articulated gripping element;

said articular joints configured in such a way that, if the tendon is released by the winding drum in said release condition, the phalanxes rotate about respective articular joints and move the articulated gripping element from the actual gripping bow-shaped position to the extended position.

In an aspect of the invention, the proximal phalanx is configured to allow an articulated gripping element to rotate about a rotation axis orthogonal to the longitudinal axis of the belt-like support, in order to allow the articulated gripping element to be wound like a bracelet or a belt in a rest bow-shaped position about said part of the user's body when the winding drum is in the release condition, wherein a passive-lock mechanism is also provided configured for blocking the articulated gripping element in the rest bow-shaped position.

The possibility of winding the articulated gripping element like a bracelet or a belt when the winding drum is in the release condition, i.e. when the articulated gripping element does not receive a driving power from the motor unit, along with the passive-lock mechanism, prevents the risk of fastening it too tight and possibly causing pain or injury to the part of the body about which the articulated gripping element is wound in the rest bow-shaped position, which occurs by the prior art devices.

Another drawback of the prior art that is overcome by the invention is that, if the drive breaks down and stops, the articulated gripping element can always be removed from the part of the body about which it is wound in the rest bow-shaped position.

Moreover, the possibility of the proximal phalanx to rotate also about a second axis, orthogonal to the longitudinal axis of the belt-like support, makes it possible to fit the device like a bracelet on a human limbs, for example about the wrist, when it is not used, which prevents any hindrance to the user's with normal activities.

Moreover, the possibility of actuating all the movements of the device by a single actuator, through at least one tendon, makes the device extremely light and easily to wear for the user.

Advantageously, the flexible articular joints are configured to be elastically loaded by said flexion movement, thereby accumulating elastic energy to be released for causing an extension movement opposite to said flexion movement.

Advantageously, the articulated gripping element comprises modules including stiff parts and flexible parts. These modules are preferably connected to each other without screws or other passive elements, preferably by flexible parts arranged to slide within the stiff parts. More in detail, in an advantageous exemplary embodiment, said articular joints are manufactured from an elastic body, in particular made of an elastomeric material, consisting of a flexible lamina having two prismatic end portions, the phalanxes providing a cooperating portion having the shape of a prismatic groove such that prismatic portions of an articular joint can be received into respective prismatic grooves of two adjacent phalanxes, so as to provide a kinematic chain that forms the articulated gripping element.

This way, the flexible articular joints can be elastically loaded due to the flexion movement, thus accumulating elastic energy that can be used for an extension movement opposite to the flexion movement. Due to the elasticity of the articular joints, after a flexion movement, by releasing the tendon of actuation, the articulated gripping element does not remain in the gripping bow-shaped position, but returns to the extended position.

Moreover, the flexibility of the articulated gripping element structure makes it possible to wind it about an object that is held or manipulated.

The motor unit can comprise a conventional electric motor rigidly connected to the winding drum through a drive shaft. In this case, the actuation condition and the release condition of the device can correspond to conditions in which this conventional motor is running or is still, respectively. A case can also be provided, in which the electric motor is selectively connectable with the winding drum through friction means or the like, where the linking/disconnection of the winding drum from the electric motor start the actuation condition and the release condition, respectively, in a motion condition of the motor.

In another aspect of the invention, the motor unit comprises a mechanically loaded motor member. This way, electric/electronic actuation parts are not present, therefore the invention is adapted to work in a wet or underwater environment, without requiring particularly hermetic protections for the components.

In particular, the mechanically loaded motor member is a spring mechanically loaded motor member, comprising a loadable spring, a loading member arranged to load the spring, and a spring release member arranged to release the spring, and wherein a member is provided for mechanically connecting/disconnecting the mechanical drive to/from the winding drum, in order to obtain said actuation condition and said release condition, respectively, wherein the articulated gripping element is arranged to take the extended position when the spring is loaded, and a gripping bow-shaped position, when the spring is substantially released. This way, in order to grip an object by the articulated gripping element, the user can actuate the spring release member, and bring the articulated gripping element from the extended position to the gripping bow-shaped position about the object. The spring can be loaded when the motor unit is switched off by the winding drum, i.e. in the release condition, for example, when the articulated gripping element is arranged in the rest bow-shaped position.

As an alternative, the mechanically loaded motor member is a friction mechanically loaded motor member, wherein the motor unit comprises:
  a crank device connected to an actuation shaft of the drive, configured in such a way that a rotation of the crank in a predetermined rotation direction brings the articulated gripping element from the extended position to the gripping bow-shaped position;
  an internal releasable brake unit, configured for retaining the articulated gripping element in the gripping bow-shaped position;
  a brake release means for releasing the internal brake unit of the transmission;
such that, by operating said brake release means, the articulated gripping element returns from the actual gripping bow-shaped position to the extended position, in particular due to an elastic recovery of said joints of said articular joints.

Preferably, a proximal joint located between the proximal phalanx and the support base is configured for orienting the rotation axis of the articulated gripping element between a rearward inclination and a forward inclination with respect to a direction normal to said support base, i.e. for orienting it forwards or backwards with respect to the longitudinal axis of the device and, accordingly, of the limb on which the device is fitted. The proximal joint can comprise a stationary part integral to the support base and a movable part rotatably connected to the stationary part.

In an exemplary embodiment, the distal phalanx comprises or is associated to a terminal object configured to come into contact with the user's fingers and hand, and the motor unit comprises a program means configured to cause the articulated gripping element to reciprocate between an extended position and a gripping bow-shaped position, so as to train the user in an attempt to grip the terminal object. The flexibility of the structure of the articulated gripping element makes it possible to use the device as an assistance or rehabilitation device for a hand, or for the rehabilitation of an upper limb.

In exemplary specific embodiments, the device can be configured, for example, to be wound about a wrist, or an ankle, or the waist of the user, performing its own grip function, and its own function of enhancing a user's grasping capability also at body parts different from the ones that are normally used for grasping and manipulating objects.

In an exemplary embodiment, the device comprises a haptic interface that is functionally connected, in particular wirelessly, to the motor unit, this interface equipped with a ring configured to be worn on a user's member selected from the group consisting of:

a finger of a hand;

the part of the body where the belt-like support is fitted, the haptic interface comprising a device selected from the group consisting of:

a switch configured to provide an actuation signal to the motor unit;

a motor-driven unit configured to provide stimulations selected from the group consisting of: compression stimulations, shear stimulations and vibrotactile stimulations, or a combination thereof, to the user's member that is in contact with the ring.

In an exemplary embodiment, the device comprises a haptic interface that can be worn by the user and that is functionally connected, in particular wirelessly, to the motor unit, wherein the interface comprises a sensor selected from the group consisting of:

a biosignal sensor configured for receiving a biosignal from the user, in particular a biosignal generated by a muscle contraction of the user;

a sensor configured for detecting movements and/or an orientation of the user's head;

a combination thereof, the sensor also arranged to provide an actuation signal to the motor unit. Such a biosignal sensor can be advantageously incorporated in an element arranged to be worn on the user's head of the device, for example in a hat.

In an exemplary embodiment, the device comprises a force display device, not shown, that is arranged for notifying the user of the intensity of the force exchanged with the object that is being held or manipulated. This makes it possible to provide a feedback to a user affected by hypoesthesia.

In an advantageous exemplary embodiment, the device has a symmetrical structure configured to be indifferently worn on a right limb or on a left limb of the user's body. This way, the device can be used to assist or to rehabilitate subjects with a disability involving both limbs, typically the upper right limb, but also the left one.

In an exemplary embodiment, the device comprises:

a member for receiving measurement values of a load of an object held by the articulated gripping element in the gripping bow-shaped position;

a computing means configured for determining, according to such values, at least a subsequent position of the device or a torque to be applied by the device so as to support at least one part of the load;

a means for generating the actuation signal responsive to the subsequent position or to the torque.

In particular, the member for receiving measurement values comprises a sensor configured for measuring:

an angle of at least one joint of the device;

a weight and/or a pressure and/or a force and/or a speed and/or an acceleration applied by the object held on the at least one module in said grip position.

According to another aspect, a method is described for assisting the grasping capacity by the above-described device, comprising the steps of:

receiving measurement values of a load of an object grasped by at least one module of the articulated gripping element in a grip position;

determining, according to these values, at least a subsequent position of the device or a torque to be applied by the device so as to support at least one part of the load;

generating the actuation signal according to the subsequent position or to the torque.

In particular, the step of receiving the measurement values comprises the steps of:

receiving from a sensor the measurement value associated to an angle of at least one joint of the articulated gripping element;

receiving the weight and/or the pressure and/or the force and/or the speed and/or the acceleration of the object held by one module or more in said grip position, or any combination of these values.

In particular, the step of sending the control signals comprises a step of sending the control signals to an actuator for adjusting the movement of the flexible robotic finger.

BRIEF DESCRIPTION OF THE DRAWINGS

The invention will be now shown with the following description of its exemplary embodiments, exemplifying but not limitative, with reference to the attached drawings, in which:

FIG. 4 shows the device of FIG. 1, in a rest bow-shaped configuration about a wrist, wherein a LED assembly display and a tendon winding pulley or drum are provided;

FIG. 5 shows the device of FIG. 1 in a working configuration, in particular in a gripping bow-shaped configuration to grip an object;

FIGS. 6 and 7 show the device of FIG. 1, mounted to a user's ankle, in a rest bow-shaped configuration about the ankle and in a working configuration, gripping a bottle, respectively;

FIGS. 8 and 9 show the device of FIG. 1, mounted to a user's waist, in a rest bow-shaped configuration about the waist and in a working configuration gripping a bag, respectively;

FIGS. 10-13 show the device of FIG. 1 while it is manipulating different objects, i.e. manipulating a cap of a jar, opening a cylindrical can, opening a parallelepiped can and squeezing a thin tube of toothpaste or the like, respectively;

DESCRIPTION OF PREFERRED EXEMPLARY EMBODIMENTS

Figure 1:
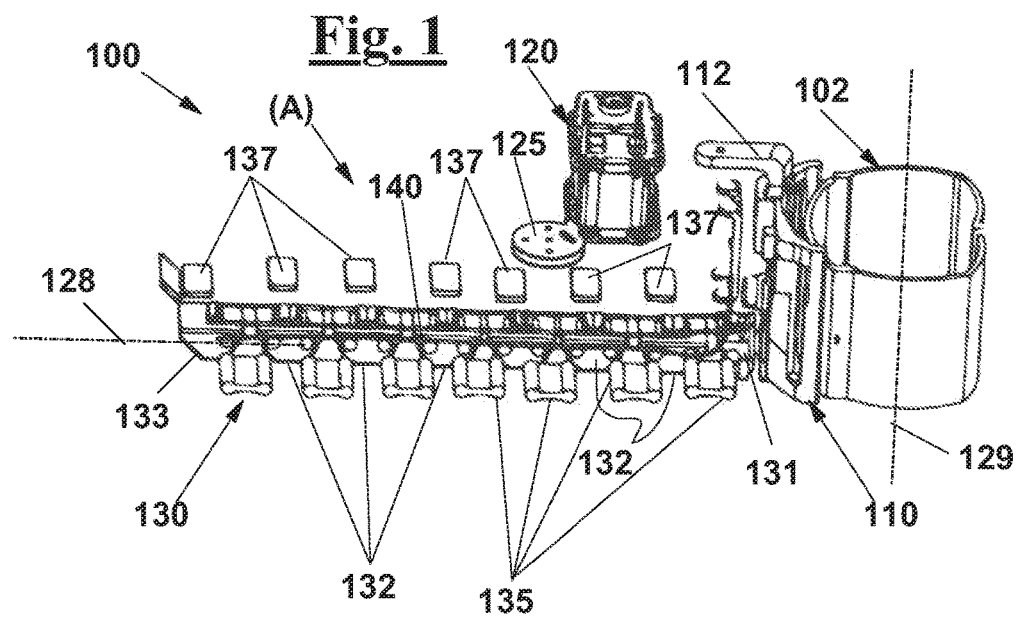
FIG. 1 is a partially exploded perspective view of a device, according to an exemplary embodiment of the invention, in which the articulated gripping element is in an extended configuration.

With reference to FIG. 1, a device 100 is described for enhancing a user's grasping capability. Device 100 mainly comprises a support base 110 and a finger, i.e. an articulated gripping element 130, which is flexible. Device 100 further comprises a belt-like support 102 for connecting the device to a part of the user's body, which is configured to be tightly fitted about a part of the body 3 such as a user's limb 1, as indicated, for example, in FIG. 2. Belt-like support 102 has an own longitudinal axis 129 that substantially coincides with the axis of the arm or of the part of the body about which belt-like support 102 is arranged. In an exemplary embodiment, as depicted, support base 110 is mounted integrally on belt-like support 102. Support base 110 is preferably configured to be brought into contact with the part of body 3 through a soft and/or high friction material, in order to prevent any unwanted relative movement, which can cause the grasped object to slip away.

Flexible finger 130 has a modular structure, comprising a plurality of stiff links or phalanxes 131, 132, 133, serially connected to each other about respective joint axes 134 parallel to one another. A proximal phalanx 131, close and fixed to support base 110, at least one medial phalanx 132, and a distal phalanx 133 are respectively.

Figure 3:
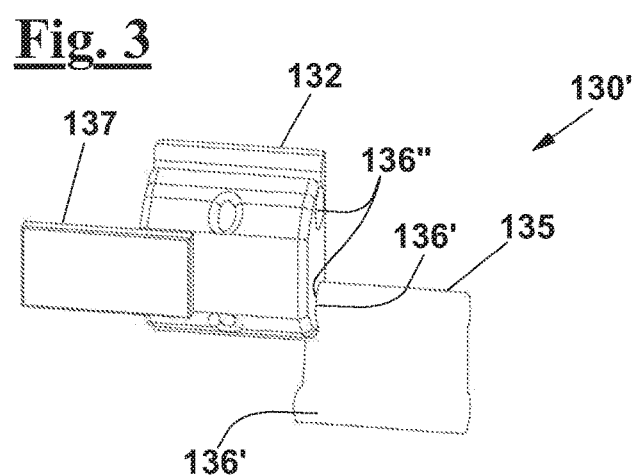
FIG. 3 is a partially exploded perspective view of a modular portion of the articulated gripping element of FIG. 1.

Phalanxes 131, 132, 133 are mutually articulated through flexible joints 135. More in detail, as shown in FIG. 3, articulated gripping element 130 has a modular structure comprising a plurality of modules 130', wherein each modular portion 130' comprises a phalanx or link 132 and a preferably elastic, flexible joint 135, consisting of a flexible lamina 135 having two prismatic or cylindrical end portions 136'. Flexible joint 135 is connected to phalanx 132 by coupling one of cooperating grooves 136', with a cooperating end portion having the shape of a prismatic or cylindrical groove 136" of phalanx 132. This also applies to respective ends of proximal and distal phalanxes 131, 133, even if FIG. 3 only shows one medial phalanx 132. This way, by connecting phalanxes 131, 132, 133 to each other, i.e. by introducing prismatic portions 136' of articular joints 135 into respective prismatic grooves 136' of one or two adjacent phalanxes, a kinematic chain is obtained that forms articulated gripping element 130 (FIG. 1).

Modules 130' are assembled to each other by causing flexible part 135 to slide within stiff part 131, 132, 133. This assembly procedure is much easier than the one provided by the prior art, and does not require any screw or passive element for joining modules 130'.

Advantageously, as shown in the same FIG. 3, padding elements 137 can be provided that are soft but provide a high friction coefficient against the skin, and that are arranged so as to form corresponding zones of contact with the objects held and possibly manipulated. For example, padding elements 137 can be connected to links 131, 132, 133 in order to increase the friction at possible contact zones 137. For instance, elements 137 can comprise a flexionally elastic plate 137, made of a resilient material such as rubber.

Figure 21:
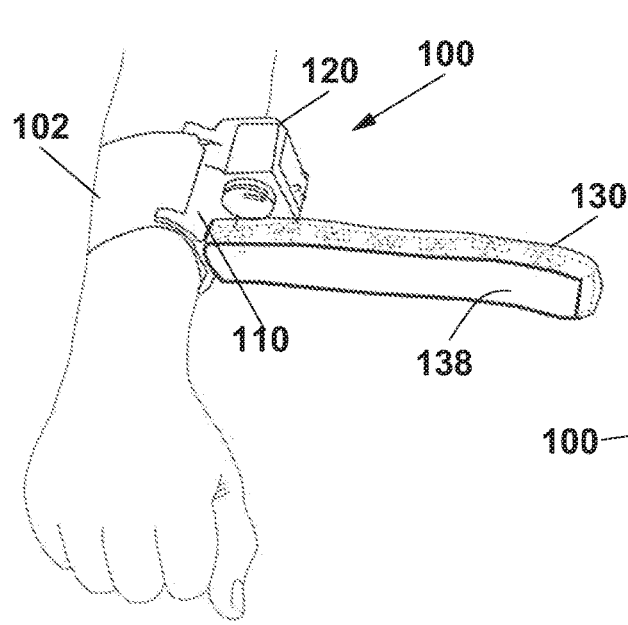
FIG. 21 shows an exemplary embodiment of the device of FIG. 1 in which the articulated gripping element has a coating layer of a material arranged to cause a predetermined friction with a manipulated object.

As shown in FIG. 21, the face of articulated gripping element 130 arranged to come into contact with an object to be manipulated 9, shown for example in FIGS. 5-7, can be coated with a coating layer 138 made of a material having a predetermined friction coefficient, such as silicone rubber, skin, tissue, in order to firmly grasp object 9. Advantageously, coating layer 138 is releasably applied on articulated gripping element 130, in order to assist its replacement for wear or according to a user's requirement.

Figure 2:
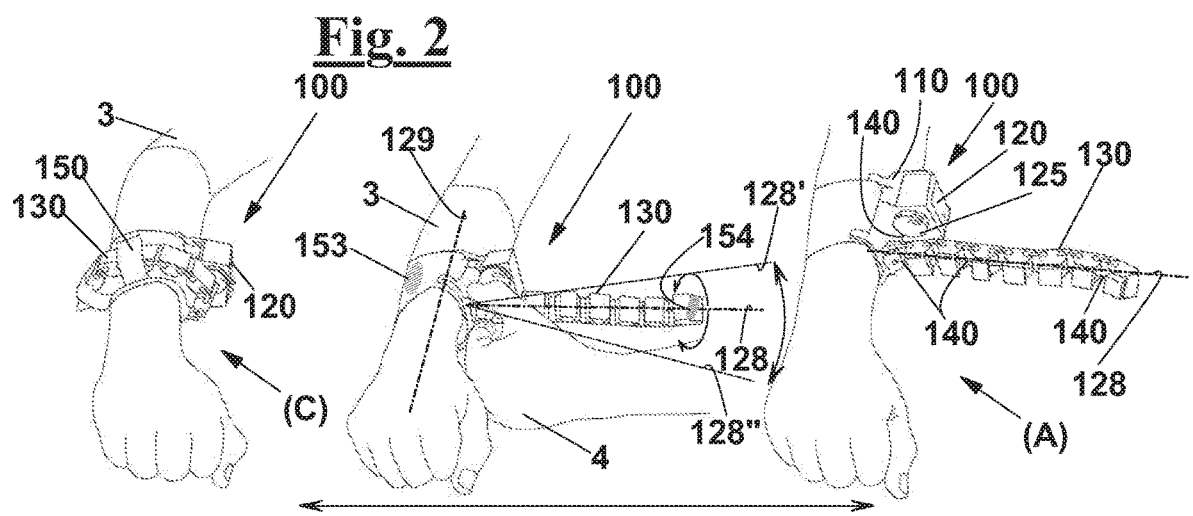
FIG. 2 shows an actuation step of the device of FIG. 1, to move it from a rest bow-shaped configuration to a working configuration, in particular in the extended configuration as shown in FIG. 1, or vice-versa.

Device 100 also comprises a motor unit 120 fixedly mounted, for instance, to a bracket 112 extending from support base 110. Motor unit 120 has a winding pulley or drum 125, shown in FIG. 4, which is fitted on an actuation shaft 124 and is configured to wind up or to unwind at least one tendon 140 (FIGS. 1 and 2). In particular, tendon 140 is in part wound on winding drum 125 and in part extends along articulated gripping element 130, through phalanxes or link 131, 132, 133 and articular joints 135. In order to provide the user with a visual feedback of the selected controls, a LED assembly display 127 can be provided, for instance, on a box of motor unit 120.

Tendon 140 is arranged in such a way that, in an actuation condition, i.e. when motor unit 120 is functionally connected to winding pulley 125, a pull action on tendon 140 by winding drum 125, causes phalanxes 131, 132, 133 to rotate about respective joint axes 134, defined, for example, by the deformation of articular joints 135, and causes articulated gripping element 130 to move from an extended position (A), as shown in FIG. 1, to a gripping bow-shaped position (B), as shown, for example, in FIG. 5, thus obtaining a flexion movement of articulated gripping element 130.

Articular joints 135 are also configured in such a way that, in a release condition, i.e. when motor unit 120 is not functionally connected to winding pulley 125, i.e. when motor unit 120 is not connected with pulley 125 and/or is still, a release of tendon 140 by winding drum 125 allows phalanxes 131, 132, 133 to rotate about respective articular joints 135 in such a way that articulated gripping element 130 moves from actual gripping bow-shaped position (B) to the extended position (A), i.e. it carries out an extension movement, opposite to the above described flexion movement. This can be obtained by rotating winding drum 125 in the unwinding direction, upon which articulated gripping element 130, instead of remaining in gripping bow-shaped position (B), returns to the extended position (A), so performing an extension movement, due to the elasticity of articular joints 135.

In particular, flexible articular joints 135 can be configured to be elastically loaded by the flexion movement, thus accumulating elastic energy to be released for performing an extension movement opposite to the flexion movement.

The motor unit or actuator 120 is therefore configured for causing the whole articulated gripping element 130 to move through pulley 125 and tendon 140. For example, holes are made through links 131, 132, 133 through which actuated tendon 140 is arranged. Tendon 140 is therefore arranged throughout finger 130 and is fastened at an own end 141, to the tip of finger 130, i.e. to distal phalanx 133, and at opposite ends 142 to winding pulley or drum 125.

Single-actuator 120 flexible articulated gripping element 130, underactuated by a tendon 140, is therefore lighter than the prior art devices, in which a plurality of actuator is arranged at the joints of the robotic finger. Moreover, in order to minimize the load acting on the arm or other part 3 of the user's body, only device 100 and its own actuator 120 are arranged on arm 3 or on the other part 3 of the body. This solution also reduces the encumbrance of device 100, for example, at arm 3.

Moreover, articulated gripping element 130, which comprises flexible joints 135, increases the strength of device 100 with against unwanted contacts with the environment, with respect to the prior art devices. Moreover, by flexible joints 135 a soft structure is obtained that allows a safer interaction with the user.

In an alternative exemplary embodiment, not shown, phalanxes 131, 132, 133 can be connected to each other in an articulated way by articular joints having a different shape, for example by hinges, parallelograms, etc., and the drum 125 can comprise two tendons 140 that are wound in a direction opposite to each other and that act as an agonist tendon and an antagonist tendon, in a way that is well known form other robotic devices and, therefore, is not described more in detail herein.

As shown in FIGS. 2 and 4, according to an aspect of the invention, proximal phalanx 131 is configured for causing articulated gripping element 130 to rotate about a rotation axis 128 orthogonal to longitudinal axis 129 of belt-like support 110, in order to allow articulated gripping element 130 to be wound in a rest bow-shaped position (C) about user's body part 3, like a bracelet or a leg band or an ankle belt. This rest bow-shaped position (C) is also shown in FIGS. 6 and 8.

Figure 20:
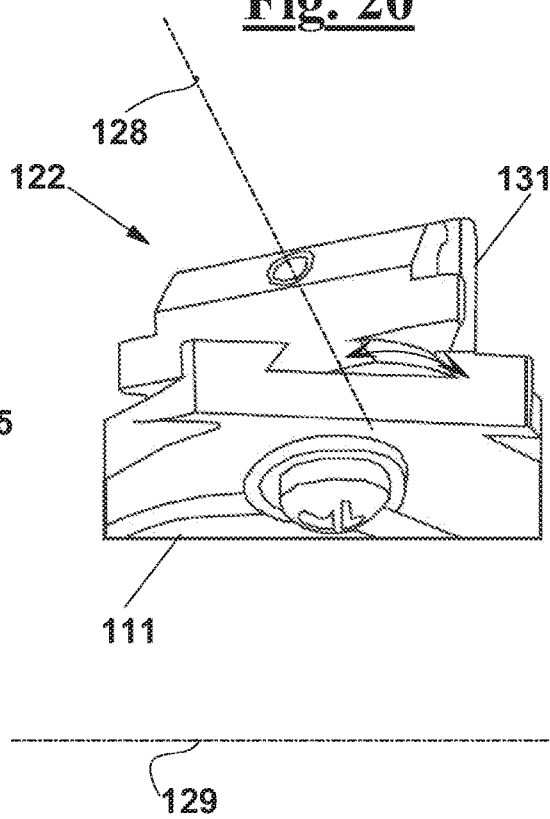
FIG. 20 shows a joint between the support base and the proximal phalanx in an exemplary embodiment of the device of FIG. 1 in which the axis of the articulated gripping element can be oriented in the plane defined with the longitudinal axis of the device itself.

The joint between proximal phalanx 131 and support base 110 is preferably configured for orienting rotation axis 128 of articulated gripping element 130 between a rearward inclination 128' and a forward inclination 128" with respect to a direction normal to the support base, i.e. for orienting it forwards or backwards with respect to longitudinal axis 129 of device 100, i.e. with respect to the longitudinal axis of arm 3. In the exemplary embodiment of FIG. 20, an orientation mechanism 122 is provided comprising a stationary part 111, integral to support base 110, and a movable part, typically proximal joint 131 itself.

In other words, device 100, in its own rest bow-shaped configuration (C), comprises a flexible articulated gripping structure or element 130 that can be wound about body part 3, respectively an arm, (FIGS. 2 and 4) an ankle (FIG. 6), the waist (FIG. 8) of the patient. This allows drastically reducing the encumbrance of device 100, when this is not used. This way, device 100 can be worn comfortably and, when it is not used, does not hinder human limb 3, on which it is mounted, nor does it reduce the workspace thereof.

As shown in FIG. 2, gripping element 130 can be caused to expand from rest bow-shaped configuration (C) until it reaches extended configuration (A), and then takes gripping bow-shaped configuration (B) about object 9, as shown in FIGS. 5-7 and 9-16. Preferably, device 100 is configured to move instantaneously from rest bow-shaped configuration (C) to the extended configuration (A).

The passage from rest bow-shaped configuration (C), for example a bracelet-like configuration, to the extended working configuration (A) or to gripping bow-shaped configuration (B), and vice-versa, can be achieved through a passive-lock mechanism 150 (FIGS. 2 and 4).

A passive-lock mechanism can be made also by providing magnetic elements or Velcro elements, or the like, at portions 153, 154 of belt 102 and of articulated gripping element 130, respectively, that are brought into contact with each other in the rest configuration (C).

As shown in FIGS. 5,7 and 9-16, device 100 is configured for gripping an object 9 by winding about it. The resilient structure of articulated gripping element 130 makes much easier to control device 100, with respect to the prior art devices. In fact, articulated gripping element 130 can adapt passively to the shape of grasped object 9. During the actuation, this shape adaptation increases the gripping capacity, compensates for the unreliability of the tactile response and improves grasp stability. For instance, the device can be used to stabilize a container 9 (FIG. 10) so that the user can screw/unscrew its cap, or to stabilize a cylindrical or prismatic can 9 (FIGS. 11 and 12) so that user 1 can open it, or to squeeze small tubes, such as a thin toothpaste tube 9 (FIG. 13), making it easier to open/close it. Device 100 can therefore be used as a compensation device for everyday operations.

The system can also be used as an active hook for supporting and preferably gripping and/or carrying objects 9. User 1 can control the device so that the latter works as a hook that grips the handle 9 of a suitcase (FIGS. 9 and 14), or that carries objects 9 in general (FIGS. 5, 7 and 15).

Device 100 can be worn also on other limbs of the body, for example on a leg for carrying a bottle 9 while walking, as shown in FIG. 7. As shown in FIGS. 8-9, an extension system can be provided such as a belt, i.e. a wearable belt that becomes an arm when required, in order to carry or to grip an object 9. According to a possible application of device 100, and to its use, suitable modifications can be made in the structure of device 100, and in the sensorization and actuation thereof, in order to make a device fulfilling the requirements of the application.

Device 100 can also be used as a device for stabilizing a structure to which it is coupled. This object requires stabilizing limb 3 for handling an object 9 with precision or for working on it, as shown, for instance, in FIG. 16. Some operations may become tiresome if prolonged. The device can bear the weight of the arm, which reduces or suppresses such a discomfort.

Figure 14:
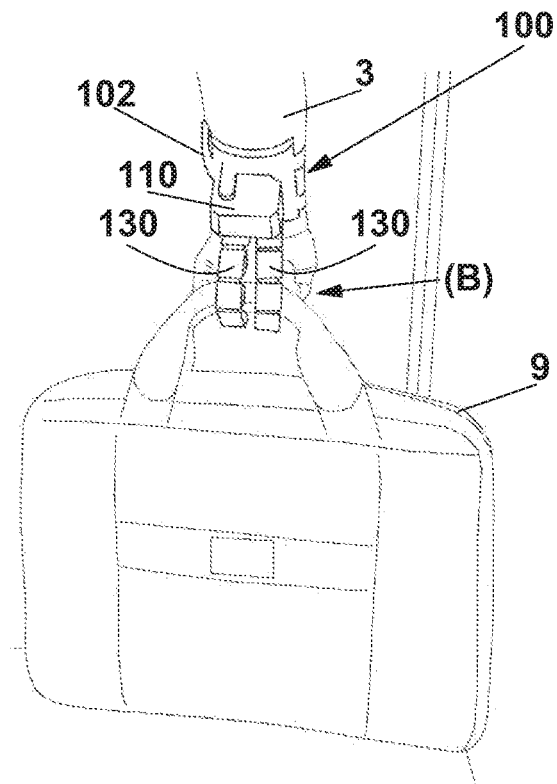
FIGS. 14 and 15 show an exemplary embodiment of a device according to the invention, in a step of gripping a bag.
Figure 15:
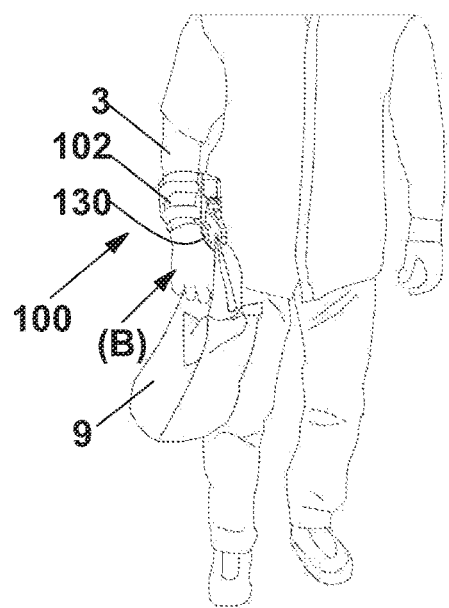

As shown in FIGS. 9,14,15, device 100 can be used to improve the grasping capacity of a hand 1 of a user having a paretic limb. In particular, device 100 and paretic hand or paretic arm 3 can act as two parts of a gripping device, such as pliers, that cooperate for grasping an object like a bag 9.

Figure 16:
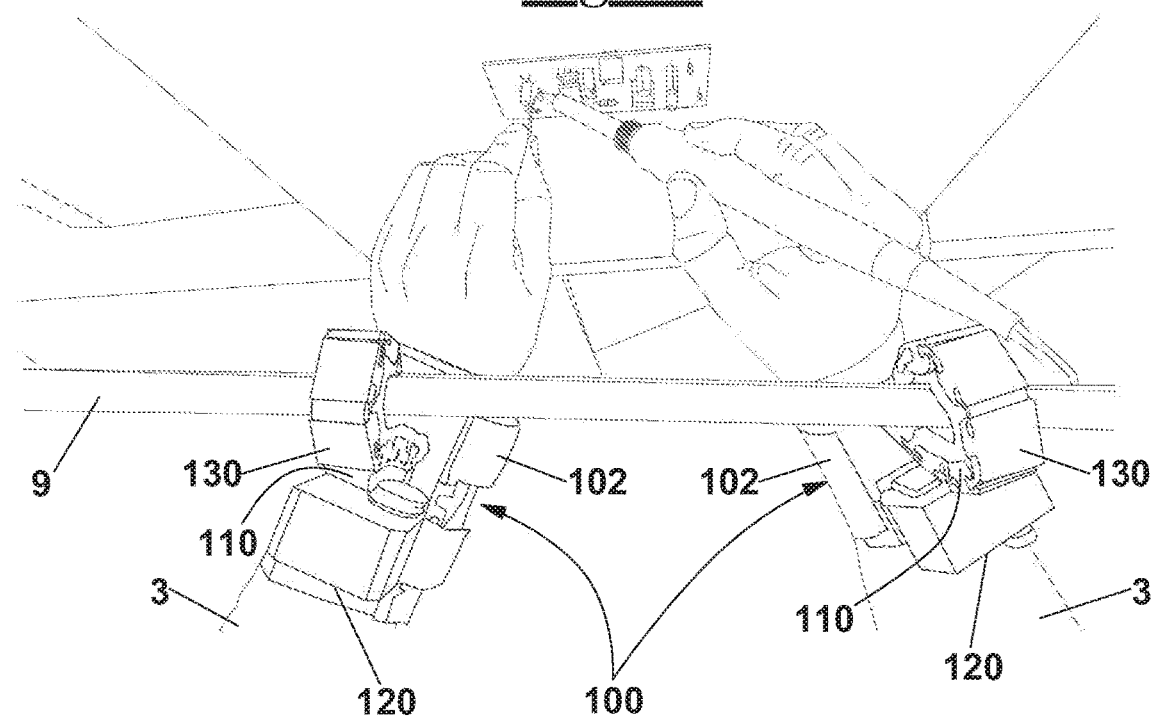
FIG. 16 shows two devices as shown in FIG. 1, which are mounted to a user's respective forearms, in respective working positions.

As shown for instance in FIGS. 14 and 16, the structure of support base 110 is preferably symmetric. This allows device 100 to be worn both on user's 1 right and left arm, without modifying device 100. Support base 110 also includes a rotatable passive-lock mechanism 150 that connects support base 110 and flexible finger 130.

Figure 19:
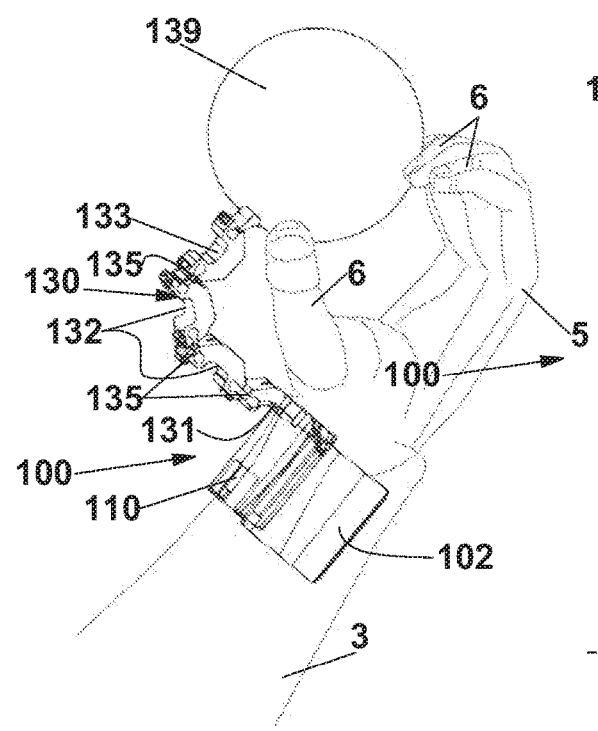
FIG. 19 shows the device of FIG. 1 in an exemplary embodiment configured for rehabilitation exercises of a patient.

As shown in FIG. 19, in an exemplary embodiment, distal phalanx 133 comprises or is associated to a terminal object 139 configured to come into contact with a user's 1 fingers 6 and hand 5, and motor unit 120 comprises a program means that causes articulated gripping element 130 to reciprocate between an extended position (A) and a gripping bow-shaped position (B), so as to train user 1 in an attempt to grip terminal object 139.

Device 100 can be used as an active rehabilitation device, whose end portion can be combined with objects that are different in stiffness and shape, and that can be actively moved by auxiliary finger 130, in order to provide different exercises for rehabilitating the hand. In particular, the device end portion can be manufactured as an active object 139 whose centre of mass is moved so as to compensate for the hinderness.

Figure 22:
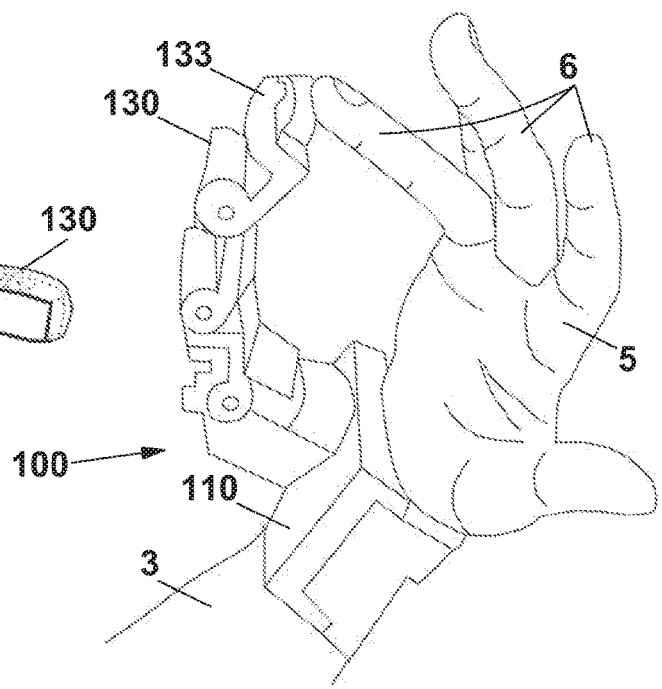
FIG. 22 shows the device of FIG. 1 engaging a user's finger for a rehabilitation exercise and/or for measuring a force.

In an exemplary embodiment, device 100 has an articulated gripping element 130 configured for working as an actual robotic finger. In other words, at least one joint 135 is actuated, in order to reproduce the flexion/extension and adduction/abduction movements. Once worn on the wrist, device 100 is therefore configured for causing robotic finger 130 to perform movements in opposition to at least one finger 6 of the user's hand, as shown in FIG. 22. The device can operate in opposition to a single finger 6 of the hand.

Advantageously, device 100 is configured for modifying the stiffness of robotic finger 130 according to a prefixed training program, and/or according to the finger 6 of the hand that is used. This makes it possible to adjust the resistance opposed to the force of a single finger 6 of the hand.

Device 100 is also configured for measuring the force exerted and/or the displacement performed by fingers 6, in order to follow the progress made by a patient using the device and in order to adapt the rehabilitation software to the results of the measurements.

In the exemplary embodiment of FIG. 19, an object 139 is connected to the end portion of device 100. The device can be configured for measuring displacements of object 139 in grip condition, so as to the progresses made by the user. As an alternative, or in addition, the device can be configured for actively displacing object 139, which is connected to its end portion. This way, by applying a force directly on object 139, it is possible to improve the user's capacity to overcome the hindrance to grip the object in a predetermined direction. Even in this case, different rehabilitation software programs can be produced to follow the user's progress.

Since the device is easy to use and comfortable to wear, it can be also utilized for purposes different from rehabilitation.

Figure 23:
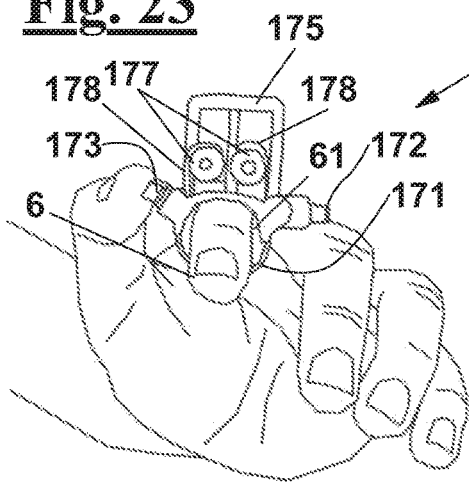
FIGS. 23-25 show a haptic device that can be worn on a finger or on a wrist, and that can be used as an interface of the device of FIG. 1, in order to control the movements thereof and/or to provide haptic data to the user.
Figure 24:
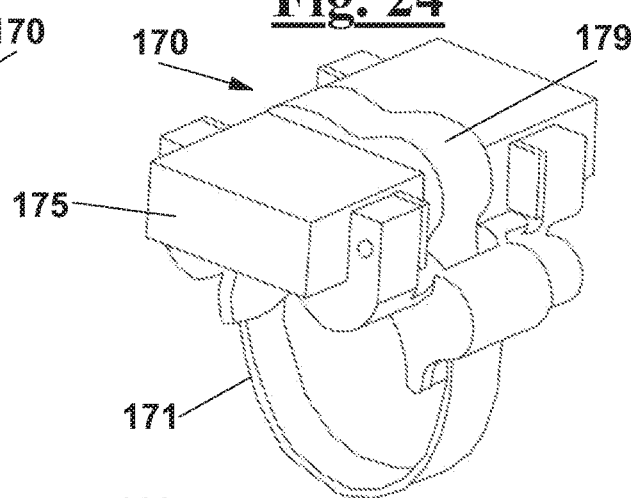
Figure 25:
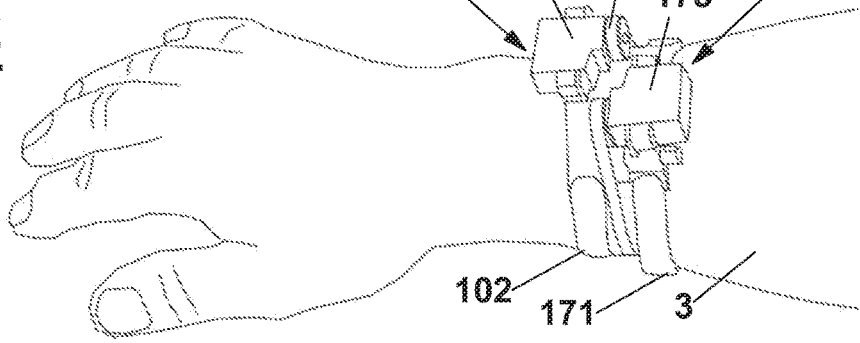

With reference to FIGS. 23-25, a wearable haptic interface 170 is described that can be used as an interface of device 100, in order to control the movement thereof and/or to provide haptic data from robotic finger 130 to user 1. Wearable haptic interface 170 is configured to be fitted on a finger 6 of user's 1 hand (FIG. 23), typically at the proximal phalanx, or on the limb itself, where device 100 is arranged, i.e. on user's 1 arm 3 (FIG. 25). In an exemplary embodiment, wearable haptic interface 170 comprises a ring 171 and at least one switch 172, 173 arranged on ring 171, through which user 1 can control the movements of robotic finger 130. In an exemplary embodiment, haptic interface 170 can provide stimulations like normal forces, or cause skin stretching, or provide vibrotactile stimulations to finger 6 of the user's hand or to user's arm 3, returning this way data of the forces applied by robotic finger 130 on a grasped object 9. Haptic interface 170 can also return data concerning the status of robotic finger 130 through vibrations, for instance, contact/non-contact conditions with object 9, achieved force/torque values etc.

Haptic interface 170 can comprise a stationary part 175 and actuators or motors 176 integral to the stationary part, pulleys 177, and fabric pieces 178 for applying the stimulations to finger 6 of the hand or to arm 3, or to a different other part of the body. A vibrating motor, not shown, can be incorporated in haptic interface 170 for providing vibrotactile stimulations. A tape hook-loop 179 is provided in order to fasten haptic interface 170 to finger 6 of the hand or to arm 3.

In order to provide the haptic feedback forces to body part 3,6, two motors 176 rotate in opposite directions with respect to each other, so that fabric piece 178 is stretched and applies a normal force on body part 3,6. On the contrary, if motors 176 rotate in the same direction, fabric piece 178 applies a shear force to body part 3,6.

Figure 17:
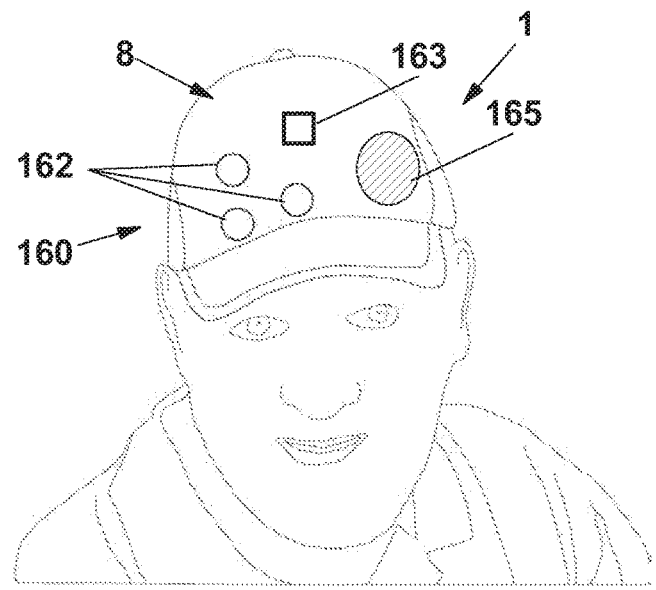
FIG. 17 shows a biosignal interface comprising sensors for controlling the movement of a user who uses the device of FIG. 1.

As shown in FIG. 17, device 100 may have a haptic interface 160 configured for receiving displacement signals or biosignals, such as electromyographic (EMG) or electroencefalographic signals, generated by user's 1 head or at user's 1 head, in order to use the displacement signals and/or the electromyographic signals to produce actuation signals for motor unit 120, and to control the flexion and extension movement of robotic finger 130 by the motor unit.

In the exemplary embodiment of FIG. 17, haptic interface 160 can be incorporated in a hat 8 or in an equivalent support.

In particular, haptic interface 160 comprises a MARG sensor 163 (Magnetic, Angular Rate, and Gravity) configured for detecting the orientation of user's 1 head, and so the changes thereof, and electromyographic sensors in the form of electrodes 162 configured for measuring user's 1 muscle contractions. Preferably, three EMG electrodes are provided, two of which are connected to a signal amplifier of interface 160, not shown, while the third one is a reference electrode, in an arrangement well known to a skilled person. Interface 160 enables user 1 to operate robotic finger 130 by a movement of the head and/or by contracting the muscles of his/her head, for example the muscles of his/her forehead.

Similarly, also the sensory stimulations can be provided at user's 1 head as compression stimulations, shear stimulations and vibrotactile stimulations in general, through a portion 165 of the haptic interface.

Motor unit 120 of device 100 can therefore be controlled by an actuation signal that simplifies the interaction with user 1. The actuation signal can be generated in control interface 160 by receiving a predetermined biosignal from sensor or sensors 162.

Figure 18:
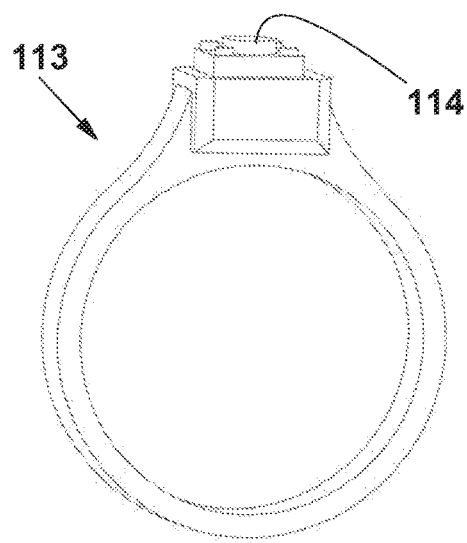
FIG. 18 shows a switch for operating the device of FIG. 1.

As an alternative, the actuation signal can be generated by operating a simple switch 114 that, as In the exemplary embodiment of FIG. 18, can be incorporated in a ring 113 also to be arranged about a patient's limb, for example close to belt 102 of device 100.

This way, device 100 can be used also by a user affected by a disability involving the upper limbs, who cannot use such interface devices as buttons and joysticks. Preferably, control interface 160 is configured to be put on by one hand, without requiring any assistance. This is useful also when a user performs operations by both hands, as shown in FIG. 16.

In a device 100 that has a haptic interface 160 or 170, a calibration procedure is provided which concerns both MARG sensor and EMG electrodes. The user must keep the head still during a predetermined period of time, for example 3 seconds, while the MARG sensor collects a number of 100 Hz samples, for example 300, for the calibration step 202, after which the current head orientation is defined as the initial orientation.

In the case of the EMG electrodes, the calibration can be based on the technique known as MVC (Maximum Voluntary Contraction). The user is required to slowly increase the muscle contractions, so as to achieve a maximum stress in a predetermined time, for example 3 seconds, in order to suitably select levels and thresholds for a correct detection.

This way, the nature of the electromyographic signals, strongly dependent on the user and on the measurement conditions, is taken into account. A control unit for haptic interface 160,170 processes the electromyographic signal, typically by filtering, rectifying, normalizing it, and by generating a steady signal that can be used for controlling device 10.

Between haptic interface 160 or 170 and device 100 a preferably wireless communication means is provided that does not hinder the movements of arm 3, on which device 100 is arranged, so as to make the system consisting of device 100 and interface 160 or 170 more comfortable to wear.

With reference to FIGS. 26-29, devices are described as further exemplary waterproof embodiments of the invention, without electric or electronic components for moving articulated gripping element 130 from extended position (A) (FIG. 1) to gripping bow-shaped position (B) (FIG. 5) and vice-versa.

Figure 26:
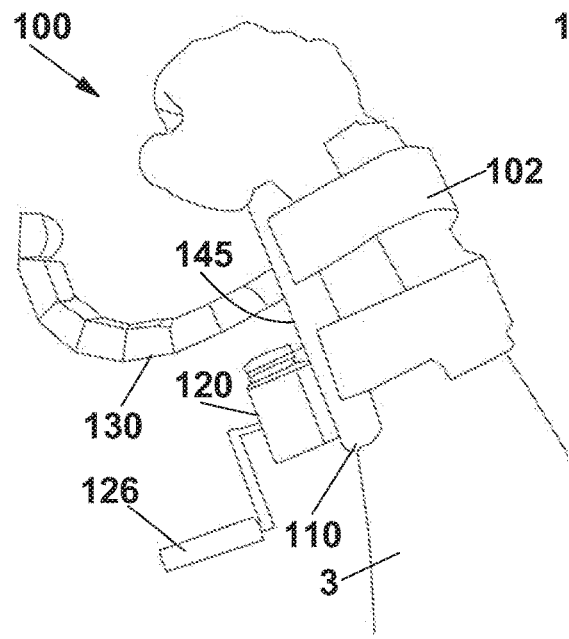
FIG. 26 shows a device, according to an exemplary embodiment of the invention, comprising a crank motor unit.

In the exemplary embodiment of FIG. 26, motor unit 120 comprises a crank 126 connected to a transmission, not shown, enclosed within a box 145, said crank 126 configured in such a way that a rotation thereof in a predetermined rotation direction moves articulated gripping element 130 from extended position (A) to gripping bow-shaped position (B). An internal releasable brake unit, not shown, is associated to the transmission and is configured for retaining articulated gripping element 130 in gripping bow-shaped position (B). The transmission is also configured for increasing the gripping force applied to the object by further rotating crank 126 in this rotation direction. Preferably, the crank can be removed from box 145, in particular when articulated gripping element 130 is in gripping bow-shaped position (B). In order to return articulated gripping element 130 to the extended position (A), a means is provided for releasing the internal brake unit of the transmission, which can have the form of a button arranged on box 145, by operating which articulated gripping element 130 returns from actual gripping bow-shaped position (B) to the extended position (A) and therefore releases object 9. This can be made through the intrinsic elasticity of articular joints 135, and/or under the action of an elastic recall means distinct from said articular joints 135.

Figure 27:
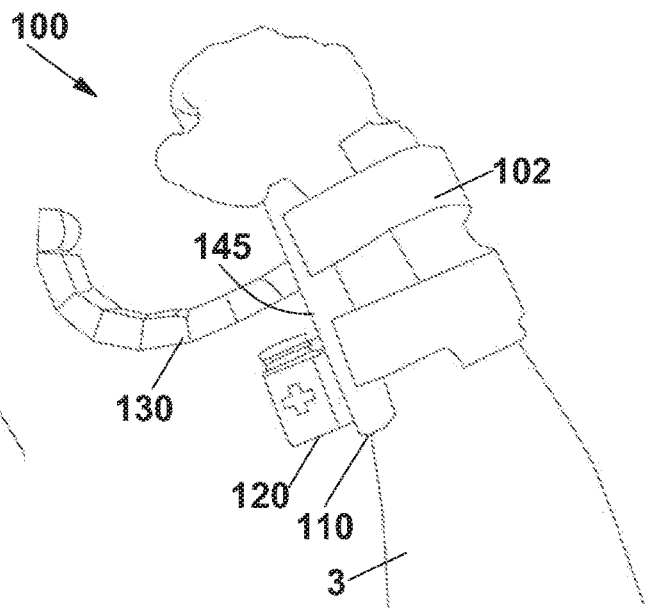
FIG. 27 shows a device, according to an exemplary embodiment of the invention, in which the motor unit comprises a mechanical spring loaded motor member.

In another exemplary embodiment, shown in FIG. 27, motor unit 120 is a spring mechanically loaded motor member comprising a loadable spring, and articulated gripping element 130 is arranged to take extended position (A) when the spring is loaded, and a gripping bow-shaped position (B) when the spring is substantially released. Motor unit 120 has a loading member arranged to load the spring and accessible from the outside of the box, arranged to be operated by a lever, not shown, which can be removed from motor unit 120, or by an outer driven rotatable device, such as a drill. Motor unit 120 also has a spring release member, preferably in the form of a key that protrudes from box 145. This way, the user can wind up the spring when articulated gripping element 130 is in rest bow-shaped position (C), for example when it is wound about arm 3 like a bracelet. Upon gripping object 9, the user brings articulated gripping element 130 to the extended position (A) against the hand and operates the spring release member in order to release the spring. Consequently, articulated gripping element 130 is bent and attains a gripping bow-shaped position (B) about object 9.

The motor unit can in any case include a conventional electric motor, not shown, which is rigidly connected to winding drum 125 through drive shaft 124. In this case, the actuation condition and the release condition of the device can correspond to conditions in which the conventional motor is working or at rest, respectively. A case can also be provided in which the electric motor can be selectively connected with the winding drum through friction means or the like, in which case the connection/disconnection of the winding drum by the electric motor starts the actuation condition and the release condition, respectively, in a motion condition of the motor.

Figure 28:
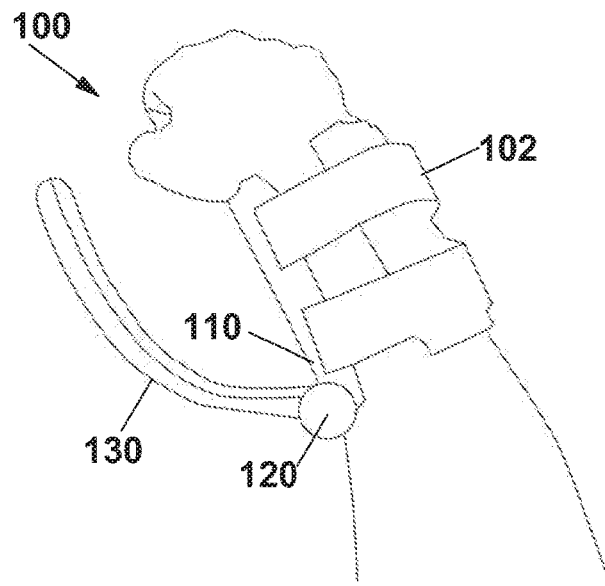
FIG. 28 shows a manually actuated device, according to an exemplary embodiment of the invention.

In a further exemplary embodiment, articulated gripping element 130 is a simple hook rotatably connected to belt-like support 102 and arranged to be grasped and manually brought from a closed rest configuration to an open grip configuration, in which it restrains the mobility of a manipulated object, as shown in FIG. 28. In this case, the face of articulated gripping element 130 intended for coming into contact with object 9 is preferably equipped with a coating layer 138 made of a material that has a predetermined friction coefficient, as described above.

The foregoing description of exemplary embodiments of the invention will so fully reveal the invention according to the conceptual point of view, so that others, using the prior art, will be able to modify and/or adapt in various applications the specific exemplary embodiments without further research and without parting from the invention, and, accordingly, it is meant that such adaptations and modifications will have to be considered as equivalent to the specific embodiments. The means and the materials to carry out the different functions described herein could have a different nature without, for this reason, departing from the field of the invention. It is to be understood that the phraseology or terminology that is employed herein is for the purpose of description and not of limitation.

The invention claimed is:

1. A device (100) for enhancing a user's (1) grasping capability, comprising:

a support (102), configured to be tightly fitted about a part of said user's (1) body (3), said support (102) having a longitudinal axis (129), an articulated gripping element (130) having a plurality of phalanxes (131, 132, 133) serially connected to each other about respective joint axes (134) parallel to one another, said phalanxes comprising a proximal phalanx (131), connected to said support (102), and a distal phalanx (133), said phalanxes (131, 132, 133) articulated to each other by articular joints (135);

a motor unit (120) fixed to said support (102);

a winding drum (125) connected to said motor unit (120) between an actuation condition and a release condition;

at least one tendon (140) partially wound on said winding drum (125), and partially extending through said phalanxes (131, 132, 133) and said articular joints (135), said tendon (140) arranged in such a way that, if said tendon (140) is pulled by said winding drum (125) in said actuation condition, said phalanxes (131, 132, 133) rotate about respective articular joints (135) and move said articulated gripping element (130) from an extended position (A) to a gripping bow-shaped position (B), causing a flexion/extension movement of said articulated gripping element (130);

said articular joints (135) configured in such a way that, if said tendon (140) is released by said winding drum (125) in said release condition, said phalanxes (131, 132, 133) rotate about respective articular joints (135), and move said articulated gripping element (130) from said gripping bow-shaped position (B) to said extended position (A), wherein said proximal phalanx (131) is configured to allow an articulated gripping element (130) to rotate about a rotation axis (128) orthogonal to said longitudinal axis (129) of said support (102), in order to allow said articulated gripping element (130) to be wound like a bracelet, or a belt, in a rest bow-shaped position (C) about said part of said user's (1) body (3) when said winding drum (125) is in said release condition, wherein a passive-lock mechanism is also provided, said passive-lock mechanism being configured to block said articulated gripping element (130) in said rest bow-shaped position (C).

2. The device (100) according to claim 1, wherein said flexible articular joints (135) are configured to be elastically loaded by said flexion movement, thereby accumulating elastic energy to be released for causing an extension movement opposite to said flexion movement.

3. The device (100) according to claim 1, wherein said articular joints (135) are manufactured from an elastic body, said elastic body consisting of a flexible lamina having two prismatic end portions, said phalanxes (131, 132, 133) providing a cooperating portion having the shape of a prismatic groove such that prismatic portions of an articular joint (135) can be received into respective prismatic grooves of two adjacent phalanxes (131, 132, 133), so as to provide a kinematic chain that forms the articulated gripping element (130).

4. The device (100) according to claim 1, wherein said motor unit (120) comprises a spring mechanically loaded motor member comprising:
- a loadable spring;
- a loading member arranged to load said spring;
- a spring release member arranged to release said spring;
- a member for mechanically connecting/disconnecting said mechanically loaded motor member to/from said winding drum (125), in order to obtain said actuation condition and said release condition, respectively,
- wherein said articulated gripping element (130) is arranged to take:
- said extended position (A) when said spring is loaded, and
- a gripping bow-shaped position (B), when said spring is substantially released;
- in such a way that said user (1), in order to grip said object (9) by said articulated gripping element (130), can connect said mechanical drive with said winding drum (125) and operate said spring release member, thus bringing said articulated gripping element (130) from said extended position (A) to said gripping bow-shaped position (B) about said object (9).

5. The device (100) according to claim 1, wherein said motor unit (120) comprises a friction mechanically loaded motor member comprising:
- a crank device (126) connected to an actuation shaft (124) of said drive, configured in such a way that a rotation of the crank (126) in a predetermined rotation direction brings the articulated gripping element (130) from said extended position (A) to said gripping bow-shaped position (B);
- an internal releasable brake unit, configured for retaining the articulated gripping element (130) in said gripping bow-shaped position (B);
- a brake release means for releasing the internal brake unit of the transmission,
- such that, by operating said brake release means, the articulated gripping element (130) returns from the gripping bow-shaped position (B) to the extended position (A) due to an elastic recovery of said joints (135) of said articular joints (135).

6. The device (100) according to claim 1, wherein a proximal joint (122) located between said proximal phalanx (131) and said support base (110) is configured for orienting said rotation axis (128) of said articulated gripping element (130) between a rearward inclination (128') and a forward inclination (128") with respect to a direction normal to said support base.

7. The device (100) according to claim 6, wherein said proximal joint (122) comprises a stationary part (111) integral to said support base (110) and a movable part (131) rotatably connected to said stationary part (111).

8. The device (100) according to claim 1, wherein said distal phalanx (133) comprises or is associated to a terminal object (139) configured to come into contact with the user's (1) fingers (6) and hand (5), and said motor unit (120) comprises a program means configured to cause said articulated gripping element (130) to reciprocate between an extended position (A) and a gripping bow-shaped position (B), so as to train said user (1) in an attempt to grip said terminal object (139).

9. The device (100) according to claim 8, comprising a force display device arranged for notifying said user of an intensity of a force exchanged with said object.

10. The device (100) according to claim 1, comprising a wearable haptic interface (170) that is functionally connected to said motor unit (120), wherein said haptic interface (170) comprises a ring (171) configured to be worn on a member (3, 6) of said user (1), said member selected from the group consisting of:
- said user's (1) finger (6);
- said part of said user's (1) body (3), to which said support (102) is fitted,
- said haptic interface comprising a device, arranged on said ring (171), and selected from the group consisting of:
- a switch (172, 173) configured to provide an actuation signal to said motor unit (120);
- a motor-driven unit (176, 177, 178) configured to provide stimulations selected from the group consisting of:
- compression stimulations;
- shear stimulations;
- vibrotactile stimulations;
- a combination thereof,
- to said user's (1) member (3, 6) that is in contact with said ring (171).

11. The device (100) according to claim 1, comprising a wearable haptic interface (160) that is arranged to be worn by said user (1) and that is functionally connected to said motor unit (120), wherein said haptic interface (160) comprises a sensor selected from the group consisting of:
- a biosignal sensor (162) configured for receiving a biosignal from said user (162);
- a sensor (163) configured for detecting movements and/or an orientation of said user's (1) head;
- a combination thereof,
- said sensor (162, 163) also arranged to provide an actuation signal to said motor unit (120).

12. The device (100) according to claim 11, wherein said wearable haptic interface (160) is incorporated in an element (8) arranged to be worn on said user's (1) head.

13. The device (100) according to claim 11, wherein the biosignal is generated by a muscle contraction of said user.

14. The device (100) according to claim 1, wherein said device (100) has a symmetrical configuration so as to be indifferently wearable on a right limb, or on a left limb of said user's body (1).

15. The device (100) according to claim 1, comprising:
a sensor for receiving measurement values of a load of an object held (9) by said articulated gripping element (130) in said gripping bow-shaped position (B);
a computing means configured for determining, according to said values, at least a subsequent position of the device (100), or a torque to be applied by said device (100), so as to support at least one part of said load;
a means for generating said actuation signal responsive to said subsequent position, or to said torque.

16. The device (100) according to claim 15, wherein said sensor is configured for measuring:
an angle of at least one joint (135) of the device (100);
a weight, and/or a pressure, and/or a force, and/or a speed, and/or an acceleration applied by said object held on said at least one module (130') in said grip position.

17. A device (100) for enhancing a user's (1) grasping capability, comprising:
a support (102) configured to be tightly fitted about a part of said user's (1) body (3), said support (102) having a longitudinal axis (129),
an articulated gripping element (130) having a plurality of phalanxes (131, 132, 133) serially connected to each other about respective joint axes (134) parallel to one another, said phalanxes comprising a proximal phalanx (131), connected to said support (102), and a distal phalanx (133), said phalanxes (131, 132, 133) articulated to each other by articular joints (135);
a motor unit (120) fixed to said support (102);
a winding drum (125) connected to said motor unit (120) between an actuation condition and a release condition;
at least one tendon (140) partially wound on said winding drum (125), and partially extending through said phalanxes (131, 132, 133) and said articular joints (135), said tendon (140) arranged in such a way that, if said tendon (140) is pulled by said winding drum (125) in said actuation condition, said phalanxes (131, 132, 133) rotate about respective articular joints (135) and move said articulated gripping element (130) from an extended position (A) to a gripping bow-shaped position (B), causing a flexion/extension movement of said articulated gripping element (130);
said articular joints (135) configured in such a way that, if said tendon (140) is released by said winding drum (125) in said release condition, said phalanxes (131, 132, 133) rotate about the respective articular joints (135) and move said articulated gripping element (130) from said gripping bow-shaped position (B) to said extended position (A),
wherein said motor unit (120) comprises a spring mechanically loaded motor member comprising:
a loadable spring;
a loading member arranged to load said spring;
a spring release member arranged to release said spring;
a member for mechanically connecting/disconnecting said mechanical drive to/from said winding drum (125), in order to obtain said actuation condition and said release condition, respectively,
wherein said articulated gripping element (130) is arranged to take:
said extended position (A) when said spring is loaded, and
a gripping bow-shaped position (B), when said spring is substantially released;
in such a way that said user (1), in order to grip said object (9) by said articulated gripping element (130), can connect said mechanical drive with said winding drum (125), and operate said spring release member, thus bringing said articulated gripping element (130) from said extended position (A) to said gripping bow-shaped position (B) about said object (9).

18. A device (100) for enhancing a user's (1) grasping capability, comprising:
a support (102) configured to be tightly fitted about a part of said user's (1) body (3), said support (102) having a longitudinal axis (129),
an articulated gripping element (130) having a plurality of phalanxes (131, 132, 133) serially connected to each other about respective joint axes (134) parallel to one another, said phalanxes comprising a proximal phalanx (131), connected to said support (102), and a distal phalanx (133), said phalanxes (131, 132, 133) articulated to each other by articular joints (135);
a motor unit (120) fixed to said support (102);
a winding drum (125) connected to said motor unit (120) between an actuation condition and a release condition;
at least one tendon (140) partially wound on said winding drum (125), and partially extending through said phalanxes (131, 132, 133) and said articular joints (135), said tendon (140) arranged in such a way that, if said tendon (140) is pulled by said winding drum (125) in said actuation condition, said phalanxes (131, 132, 133) rotate about respective articular joints (135), and move said articulated gripping element (130) from an extended position (A) to a gripping bow-shaped position (B), causing a flexion/extension movement of said articulated gripping element (130);
said articular joints (135) configured in such a way that, if said tendon (140) is released by said winding drum (125) in said release condition, said phalanxes (131, 132, 133) rotate about the respective articular joints (135), and move said articulated gripping element (130) from said gripping bow-shaped position (B) to said extended position (A),
wherein said motor unit 120 comprises:
a crank device (126) connected to an actuation shaft (124) of said drive, configured in such a way that a rotation of the crank (126), in a predetermined rotation direction, brings the articulated gripping element (130) from said extended position (A) to said gripping bow-shaped position (B);
an internal releasable brake unit, configured for retaining the articulated gripping element (130) in gripping bow-shaped position (B);
a brake release means for releasing the internal brake unit of the transmission,
such that, by operating said brake release means, articulated gripping element 130 returns from the actual gripping bow-shaped position (B) to the extended position (A) due to an elastic recovery of said joints (135) of said articular joints (135).

* * * * *